United States Patent
Olejniczak et al.

(10) Patent No.: US 9,314,487 B2
(45) Date of Patent: Apr. 19, 2016

(54) METHODS FOR TREATING CARTILAGE DISORDERS, DISEASES, AND INJURIES

(71) Applicant: Stemnion, Inc., Pittsburgh, NY (US)

(72) Inventors: Donna M Olejniczak, Pittsburgh, PA (US); David L Steed, Pittsburgh, PA (US); Randall G Rupp, Swanton, VT (US); George L Sing, New York, NY (US)

(73) Assignee: STEMNION, INC., Pittsburgh, PA (US)

( * ) Notice: Subject to any disclaimer, the term of this patent is extended or adjusted under 35 U.S.C. 154(b) by 100 days.

(21) Appl. No.: 14/276,140

(22) Filed: May 13, 2014

(65) Prior Publication Data

US 2014/0341860 A1   Nov. 20, 2014

Related U.S. Application Data

(60) Provisional application No. 61/855,550, filed on May 17, 2013.

(51) Int. Cl.
*A61K 35/50* (2015.01)

(52) U.S. Cl.
CPC ..................................... *A61K 35/50* (2013.01)

(58) Field of Classification Search
None
See application file for complete search history.

(56) References Cited

U.S. PATENT DOCUMENTS

| | | | |
|---|---|---|---|
| 8,273,347 B2 * | 9/2012 | Attawia | A61K 35/28 424/93.7 |
| 2006/0222634 A1 | 10/2006 | Clarke et al. | |
| 2007/0231297 A1 | 10/2007 | Smith et al. | |
| 2009/0054339 A1 | 2/2009 | Marshall et al. | |
| 2014/0037591 A1 | 2/2014 | Wessel et al | |

OTHER PUBLICATIONS

Benz, K., et al., Eur Spine J (2012) 21:1758-1768.
Bergknut, N., et al., Spine vol. 37, No. 5, pp. 351-358, 2012.
Boeuf, S., et al., Stem Cell Research & Therapy 2010, 1:31.
Campbell, D., et al., Cells, 2012, 1:1107-1120.
Chu, C., et al., Tissue Engineering, Part B, vol. 16, No. 1, 2010, pp. 105-115.
Philip, J., et al., ePlasty, vol. 13, 2013, pp. 225-234.
Ghosh, P., et al., J Neurosurg Spine, 2012, 16:479-488.
Mayer-Wagner, S., et al., Bioelectromagnetics, 2011, 32:283-290.

* cited by examiner

*Primary Examiner* — Allison Fox
(74) *Attorney, Agent, or Firm* — Linda O. Palladino; Gail M. Kempler

(57) ABSTRACT

The invention is directed to methods for treating cartilage disorders, diseases and injuries including, but not limited to, degenerative disc disease. The invention is also directed to methods for preventing cartilage disorders and diseases including, but not limited to, degenerative disc disease. The field of the invention is further directed to reducing inflammation associated with cartilage disorders, diseases and injuries including, but not limited to, degenerative disc disease.

2 Claims, No Drawings

US 9,314,487 B2

METHODS FOR TREATING CARTILAGE DISORDERS, DISEASES, AND INJURIES

FIELD OF THE INVENTION

The field of the invention is directed to methods for treating cartilage disorders, diseases and injuries including, but not limited to, degenerative disc disease. The field of the invention is also directed to methods for preventing cartilage disorders and diseases including, but not limited to, degenerative disc disease. The field of the invention is further directed to reducing inflammation associated with cartilage disorders, diseases and injuries including, but not limited to, degenerative disc disease. The field of the invention is also directed to novel compositions useful in the methods for preventing cartilage disorders, diseases and injuries including, but not limited to, degenerative disc disease and/or treating cartilage disorders, diseases and injuries including, but not limited to, degenerative disc disease and/or reducing inflammation associated with disorders, diseases and injuries including, but not limited to, degenerative disc disease. Such methods are effected by administering to a subject suffering from such conditions, or at risk of developing such conditions, novel cellular factor-containing solution compositions (referred to herein as "CFS" compositions), including novel sustained-release cellular factor-containing solution compositions (referred to herein as "SR-CFS" compositions), including Amnion-derived Cellular Cytokine Solution (ACCS), nucleus pulposus (NP) ACCS (ACCS-NP) and annulus fibrosus (AF) ACCS (ACCS-AF) and/or cells, including Amnion-derived Multipotent Progenitor (AMP) cells, nucleus pulposus-AMP cells (AMP-NP cells), and annulus fibrosus-AMP cells (AMP-AF cells), alone or in combination with each other and/or other agents and/or treatment modalities.

BACKGROUND OF THE INVENTION

Cartilage is a flexible connective tissue found in the joints between bones, the rib cage, the ear, the nose, the bronchial tubes, the pubic symphysis, and the intervertebral discs. Cartilage is not as hard and rigid as bone but is stiffer and less flexible than tendons and ligaments. Cartilage is made by specialized cells called chondroblasts that produce a large amount of extracellular matrix composed of collagen fibers, abundant ground substance rich in proteoglycan, and elastin fibers. Cartilage is classified in three types, elastic cartilage, hyaline cartilage and fibrocartilage, which differ in the relative amounts of these three main components. Chondroblasts that get caught in the matrix are called chondrocytes. They reside in spaces called lacunae with up to eight chondrocytes per lacuna.

Unlike other connective tissues, cartilage does not contain blood vessels. The chondrocytes are supplied by diffusion, which is helped by the pumping action generated by compression of the articular cartilage or flexion of the elastic cartilage. Because it does not have a direct blood supply, compared to other connective tissues, cartilage grows and repairs much more slowly. As a result, when cartilage is injured or diseased, it is very difficult to heal. It is believed that a treatment option that could prevent the development of cartilage disorders and diseases, accelerate healing of cartilage once injured or diseased, perhaps eliminating the need for surgical intervention in severe cases, is desirable. Accordingly, it is an object of the instant invention to provide such a treatment option to subjects suffering from cartilage diseases, disorders and injuries including, but not limited to, degenerative disc disease.

BRIEF SUMMARY OF THE INVENTION

The instant invention provides novel cellular factor-containing solution (CFS) compositions, including ACCS, NP-ACCS and AF-ACCS, as well as novel cells including AMP cells, AMP-NP cells, and AMP-AF cells for use in the described methods for preventing, treating and reducing inflammation associated with cartilage diseases, disorders and injuries including, but not limited to, degenerative disc disease. The instant invention also provides novel sustained-release cellular factor-containing solution (SR-CFS) compositions, including SR-ACCS, SR-ACCS-NP and SR-ACCS-AF, for use in the methods. Because the cellular factors are present in the CFS compositions at levels comparable to physiological levels found in the body, they are optimal for use in therapeutic applications which require intervention to support, initiate, replace, accelerate, down-regulate or otherwise influence biochemical and biological processes involved in the treatment and/or healing of disease and/or injury and/or inflammation. In the case of the SR-CFS compositions, the cellular factors are released slowly over time to provide a continual, consistent physiologic level of such factors to optimize healing and/or recovery. In the case of AMP cells, AMP-NP cells and AMP-AF cells, the cells continually secrete physiological levels of such factors. Detailed information about the ACCS, SR-ACCS and AMP cell compositions used in the methods can be found in U.S. Pat. Nos. 8,058,066, 8,088,732, and 8,278,095, each of which is incorporated herein by reference.

Applicants have discovered that ACCS and AMP cells exhibit many anti-inflammatory properties as well as healing properties. It has been shown that ACCS is effective in impaired conditions. Because lack of blood supply can be considered an impaired condition, ACCS may be particularly well-suited for use in the claimed methods. ACCS and/or AMP cells would be expected to be an effective means of preventing the development of cartilage diseases, disorders and injuries, treating cartilage diseases, disorders and injuries, and reducing inflammation associated with cartilage diseases, disorders and injuries including, but not limited to, degenerative disc disease. ACCS-NP and ACCS-AF are made by culturing AMP cells under specific conditions such that they develop either a NP cell- or AF cell-like phenotype, including secreting substances that are normally secreted by NP cells and AF cells into the culture medium, which is then collected and used in the methods of the invention.

As described in detail below, degenerating disc disease (DDD) is a major health problem. The intervertebral disc (IVD) is a complex structure comprising a central gelatinous nucleus pulposus (NP), which is rich in proteolycans and Collagen II, encased by a ligamentous annulus fibrosus (AF) which contains concentrically arranged lamellae, Collagen I and Collagen II and Elastin fibers which help to withstand compressive forces, and inferiorly and superiorly positioned cartilaginous endplates (EP) which provide continuity. The IVD is mostly avascular and aneural, and depends on the blood supply at the margins of the discs (EP) for nutrients and, for neural supply, the sinovertebral nerves extending only to the outer AF.

Inflammation appears to be a critical component of DDD. Degeneration is associated with inflammatory mediators and cytokines that are known to increase catabolic factors such as matrix metalloproteinases (MMPs) and suppress anabolic factors that lead to proteoglycan and collagen production. This abnormal local production of matrix remodeling enzymes is believed to lead to the progression of IVD degeneration. The resultant loss of proteoglycans and the consequential dehydration of the disc adversely affect its load-bearing capacity. It has also been suggested that pro-inflammatory cytokines sensitize the nerves in the IVD, thus triggering pain. In the normal intervertebral disc, the nucleus pulposus and inner annulus fibrosus are devoid of nerves. The superficial (believed to be outer 3 layers) of normal AF have sensory nerve endings with a depth of penetration of about 3 mm (See "The nerve supply of the lumbar intervertebral disc", M. A. Edgar, The Journal of Bone & Joint Surgery, Vol 89-B, No. 9, September 2007). In the damaged or diseased disc the innervation may be increased in number and depth. The inflammatory cytokine, IL-17, has been specifically isolated in approximately 70% of tissue samples from DDD sufferers but is rarely found in normal tissue.

Acknowledgment of the role of inflammation in the etiology of DDD has led to the suggested use of Rhein (RH) for treatment. This anthraquinone molecule is capable of inhibiting an inflammatory response and enhancing the synthesis of matrix components, diminishes pain and results in functional improvement in osteoarthritis. This activity is thought to be due to the ability of RH to inhibit IL-1-induced apoptosis and secretion of MMPs, which, as described above, have been implicated in breakdown of the disc extracellular matrix.

Applicants have discovered that ACCS, which is comprised of the secretory products of AMP) cells, has anti-inflammatory properties, that it contains many different cytokines and growth factors at physiologic quantities, that it contains the MMP inhibitors TIMP-1 and TIMP-2, and that it has been found to be effective at reducing apoptosis-induced cell death as well as preventing such cell death.

Applicants have demonstrated that ACCS exhibits strong anti-inflammatory effects, in both in vitro and in vivo models. In cell culture experiments, treatment of peripheral blood mononuclear cells with ACCS significantly inhibited lipopolysaccharide induction of both TNFα and PGE2 (ranging from 70 to 94% reduction). These mediators may also play a role in DDD-related inflammation, thus providing rationale for the use of ACCS and/or AMP cells for treatment of such conditions. Steroids are commonly injected either epidurally or intradiscally to treat DDD. ACCS may be an equally effective anti-inflammatory injected through either route, but its combined properties (decreasing matrix breakdown and potential anabolic related activity) may be most effective when it is injected intradiscally. Also, unlike steroids which can only be used for limited amounts of time due to side effects, ACCS does not appear to be limited in how often or how long it can administered.

The anti-inflammatory activity of ACCS has also been demonstrated in a rabbit model of periodontitis (see Examples 1 and 2 below).

Further evidence that ACCS has anti-inflammatory properties has come from preclinical data using an established preclinical model of skin inflammation in mice in which the protein kinase C activator, 12-O-tetradecanoylphorbol-13-acetate (TPA), is applied to normal mouse ears. In that model system, ACCS was shown to cause significant reduction in TPA-induced inflammation in skin (see Examples 3 and 4 below). In addition to its anti-inflammatory properties, ACCS also contains cytokines, growth factors and MMP inhibitors, which may be useful in the treatment of DDD by 1) increasing the survival of NP cells by exposure to protective or proliferative factors, 2) blocking the loss of NP cells caused by apoptosis, oxidative stress, and/or inflammation, 3) up-regulating the production of key matrix proteins (e.g. aggrecan) by surviving NP cells, and 4) reducing inflammation induced by pro-inflammatory cytokines (IL-1 and TNF-α) and associated tissue breakdown by matrix metalloproteinases (MMPs). Accordingly, ACCS represents a novel biologic therapeutic option for the treatment of DDD and perhaps other cartilage diseases, disorders and injuries in which inflammation is causing a detrimental effect. In addition to these important properties of ACCS, ACCS-NP and ACCS-AF will possess a profile of components, including extracellular matrix components, particularly well-suited for use in the claimed methods.

Given the anti-inflammatory activity of ACCS and the fact that it contains cytokines, growth factors and MMP inhibitors, all of which may be relevant to maintaining the integrity of the IVD matrix, ACCS represents a novel biologic therapeutic option for the treatment of DDD and perhaps other cartilage diseases, disorders and injuries in which inflammation is causing a detrimental effect. In addition to these important properties of ACCS, ACCS-NP and ACCS-AF will possess a profile of components, including extracellular matrix components, particularly well-suited for use in the claimed methods.

Accordingly, a first aspect of the invention is a method for treating cartilage diseases, disorders and injuries in a patient in need thereof comprising administering to the patient a therapeutically effective amount of a composition selected from the group consisting of a CFS composition, Amnion-derived Multipotent Progenitor (AMP) cells, AMP-NP cells and AMP-AF cells.

A second aspect of the invention is a method for reducing inflammation associated with cartilage diseases, disorders and injuries in a patient in need thereof comprising administering to the patient a therapeutically effective amount of a composition selected from the group consisting of a CFS composition, AMP cells, AMP-NP cells and AMP-AF cells such that inflammation associated with the cartilage disease, disorder or injury is reduced.

A third aspect of the invention is a method for preventing cartilage diseases and disorders in a patient at risk for developing a cartilage disease or disorder comprising administering to the patient a therapeutically effective amount of a composition selected from the group consisting of a CFS composition, AMP cells, AMP-NP cells and AMP-AF cells.

A fourth aspect of the invention is a method for promoting the growth or enhancing the survival of nucleus pulposus (NP) cells in a degenerating intervertebral disc comprising administering to the degenerating intervertebral disc a therapeutically effective amount of a composition selected from the group consisting of a CFS composition, AMP cells, AMP-NP cells and AMP-AF cells.

A fifth aspect of the invention is a method for preventing degradation of extracellular matrix in cartilage comprising administering to the cartilage a therapeutically effective amount of a composition selected from the group consisting of a CFS composition, AMP cells, AMP-NP cells and AMP-AF cells.

One embodiment of aspects one-five is one in which the CFS composition is selected from the group consisting of ACCS, ACCS-NP and ACCS-AF. In another embodiment the CFS compositions are formulated for sustained-release. In another embodiment of aspects one-five, the cartilage disease, disorder or injury is selected from the group consisting of osteoarthritis, rheumatoid arthritis, gouty arthritis, psoriatic arthritis, intervertebral disc herniation, degenerative disc disease, spinal stenosis, lumbar scoliosis, chondrodystrophies, traumatic rupture or detachment, achondroplasty, costochondritis, relapsing polychondritis destruction, and ankylosing spondylitis.

A fourth aspect of the invention is a composition comprising AMP-NP cells.

A fifth aspect of the invention is a composition comprising AMP-AF cells.

A sixth aspect of the invention is a composition comprising ACCS-NP.

A seventh aspect of the invention is a composition comprising ACCS-AF.

Other aspects and embodiments, while not explicitly stated, are understood to be contemplated by the instant invention.

Definitions

As defined herein "isolated" refers to material removed from its original environment and is thus altered "by the hand of man" from its natural state.

As used herein, the term "protein marker" means any protein molecule characteristic of the plasma membrane of a cell or in some cases of a specific cell type.

As used herein, "enriched" means to selectively concentrate or to increase the amount of one or more materials by elimination of the unwanted materials or selection and separation of desirable materials from a mixture (i.e. separate cells with specific cell markers from a heterogeneous cell population in which not all cells in the population express the marker).

As used herein, the term "substantially purified" means a population of cells substantially homogeneous for a particular marker or combination of markers. By substantially homogeneous is meant at least 90%, and preferably 95% homogeneous for a particular marker or combination of markers.

The term "placenta" as used herein means both preterm and term placenta.

As used herein, the term "totipotent cells" shall have the following meaning In mammals, totipotent cells have the potential to become any cell type in the adult body; any cell type(s) of the extraembryonic membranes (e.g., placenta). Totipotent cells are the fertilized egg and approximately the first 4 cells produced by its cleavage.

As used herein, the term "pluripotent stem cells" shall have the following meaning Pluripotent stem cells are true stem cells with the potential to make any differentiated cell in the body, but cannot contribute to making the components of the extraembryonic membranes which are derived from the trophoblast. The amnion develops from the epiblast, not the trophoblast. Three types of pluripotent stem cells have been confirmed to date: Embryonic Stem (ES) Cells (may also be totipotent in primates), Embryonic Germ (EG) Cells, and Embryonic Carcinoma (EC) Cells. These EC cells can be isolated from teratocarcinomas, a tumor that occasionally occurs in the gonad of a fetus. Unlike the other two, they are usually aneuploid.

As used herein, the term "multipotent stem cells" are true stem cells but can only differentiate into a limited number of types. For example, the bone marrow contains multipotent stem cells that give rise to all the cells of the blood but may not be able to differentiate into other cells types.

As used herein, the term "extraembryonic tissue" means tissue located outside the embryonic body which is involved with the embryo's protection, nutrition, waste removal, etc. Extraembryonic tissue is discarded at birth. Extraembryonic tissue includes but is not limited to the amnion, chorion (trophoblast and extraembryonic mesoderm including umbilical cord and vessels), yolk sac, allantois and amniotic fluid (including all components contained therein). Extraembryonic tissue and cells derived therefrom have the same genotype as the developing embryo.

As used herein, the term "extraembryonic cytokine secreting cells" or "ECS cells" means a population of cells derived from the extraembryonic tissue which have the characteristics of secreting a unique combination of physiologically relevant cytokines in a physiologically relevant temporal manner into the extracellular space or into surrounding culture media and which have not been cultured in the presence of any animal-derived products, making them and cell products derived from them suitable for human clinical use. In a preferred embodiment, the ECS cells secrete the cytokines VEGF, Angiogenin, PDGF and TGFβ2 and the MMP inhibitors TIMP-1 and/or TIMP-2. The physiological range of the cytokine or cytokines in the unique combination is as follows: ~5-16 ng/mL for VEGF, ~3.5-4.5 ng/mL for Angiogenin, ~100-165 pg/mL for PDGF, ~2.5-2.7 ng/mL for TGFβ2, ~0.68 µg/mL for TIMP-1 and ~1.04 µg/mL for TIMP-2.

As used herein, the term "amnion-derived multipotent progenitor cell" or "AMP cell" means a specific population of ECS cells that are epithelial cells derived from the amnion. In addition to the characteristics described above for ECS cells, AMP cells have the following characteristics. They have not been cultured in the presence of any animal-derived products, making them and cell products derived from them suitable for human clinical use. They grow without feeder layers, do not express the protein telomerase and are non-tumorigenic. AMP cells do not express the hematopoietic stem cell marker CD34 protein. The absence of CD34 positive cells in this population indicates the isolates are not contaminated with hematopoietic stem cells such as umbilical cord blood or embryonic fibroblasts. Virtually 100% of the cells react with antibodies to low molecular weight cytokeratins, confirming their epithelial nature. Freshly isolated amnion epithelial cells, from which AMP cells are selected, will not react with antibodies to the stem/progenitor cell markers c-kit (CD117) and Thy-1 (CD90).

By the term "animal-free" when referring to certain compositions, growth conditions, culture media, etc. described herein, is meant that no non-human animal-derived materials, such as non-human animal-derived serum, other than clinical grade human materials, such as recombinantly produced human proteins, are used in the preparation, growth, culturing, expansion, storage or formulation of the certain composition or process.

By the term "serum-free" when referring to certain compositions, growth conditions, culture media, etc. described herein, is meant that no animal-derived serum (i.e. no non-human animal) is used in the preparation, growth, culturing, expansion, storage or formulation of the certain composition or process.

By the term "expanded", in reference to cell compositions, means that the cell population constitutes a significantly higher concentration of cells than is obtained using previous methods. For example, the level of cells per gram of amniotic tissue in expanded compositions of AMP cells is at least 50 and up to 150 fold higher than the number of cells in the primary culture after 5 passages, as compared to about a 20-fold increase in such cells using previous methods. In another example, the level of cells per gram of amniotic tissue in expanded compositions of AMP cells is at least 30- and up to 100-fold higher than the number of cells in the primary culture after 3 passages. Accordingly, an "expanded" population has at least a 2-fold, and up to a 10-fold, improvement in cell numbers per gram of amniotic tissue over previous methods. The term "expanded" is meant to cover only those situations in which a person has intervened to elevate the number of the cells.

As used herein, "conditioned medium" is a medium in which a specific cell or population of cells has been cultured, and then removed. When cells are cultured in a medium, they may secrete cellular factors that can provide support to or affect the behavior of other cells. Such factors include, but are not limited to hormones, cytokines, extracellular matrix (ECM), proteins, vesicles, antibodies, chemokines, receptors, inhibitors and granules. The medium containing the cellular factors is the conditioned medium. As used herein, conditioned medium also refers to components, such as proteins, that are recovered and/or purified from conditioned medium or from ECS cells, including AMP cells.

As used herein, the term "cellular factor-containing solution" or "CFS" composition means a composition having physiologic concentrations of one or more protein factors. CFS compositions include conditioned media derived from ECS cells, amnion-derived cellular cytokine solution compositions (see definition below), physiologic cytokine solution compositions (see definition below), and sustained release formulations of such CFS compositions.

As used herein, the term "amnion-derived cellular cytokine solution" or "ACCS" means conditioned medium that has been derived from AMP cells or expanded AMP cells.

As used herein, the term "nucleus pulposus amnion-derived cellular cytokine solution" or "ACCS-NP" means conditioned medium that has been derived from AMP cells or expanded AMP cells that have been cultured under specific conditions such that they develop a NP cell-like phenotype (AMP-NP cells) and secrete a unique profile of components, including extracellular matrix components, into the culture medium that are particularly well-suited for use in the claimed methods. As used herein, the term "annulus fibrosus amnion-derived cellular cytokine solution" or "ACCS-AF" means conditioned medium that has been derived from AMP cells or expanded AMP cells that have been cultured under specific conditions such that they develop a AF cell-like phenotype (AMP-AF cells) and secrete a unique profile of components, including extracellular matrix components, into the culture medium that are particularly well-suited for use in the claimed methods.

As used herein, the term "physiologic cytokine solution" or "PCS" composition means a composition which is not cell-derived and which has physiologic concentrations of VEGF, Angiogenin, PDGF and TGFβ2, TIMP-1 and TIMP-2.

As used herein, the term "suspension" means a liquid containing dispersed components, i.e. cytokines The dispersed components may be fully solubilized, partially solubilized, suspended or otherwise dispersed in the liquid. Suitable liquids include, but are not limited to, water, osmotic solutions such as salt and/or sugar solutions, cell culture media, and other aqueous or non-aqueous solutions.

The term "lysate" as used herein refers to the composition obtained when cells, for example, AMP cells, are lysed and optionally the cellular debris (e.g., cellular membranes) is removed. This may be achieved by mechanical means, by freezing and thawing, by sonication, by use of detergents, such as EDTA, or by enzymatic digestion using, for example, hyaluronidase, dispase, proteases, and nucleases.

The term "physiologic" or "physiological level" as used herein means the level that a substance in a living system is found and that is relevant to the proper functioning of a biochemical and/or biological process.

As used herein, the term "substrate" means a defined coating on a surface that cells attach to, grown on, and/or migrate on. As used herein, the term "matrix" means a substance that cells grow in or on that may or may not be defined in its components. The matrix includes both biological and non-biological substances. As used herein, the term "scaffold" means a three-dimensional (3D) structure (substrate and/or matrix) that cells grow in or on. It may be composed of biological components, synthetic components or a combination of both. Further, it may be naturally constructed by cells or artificially constructed. In addition, the scaffold may contain components that have biological activity under appropriate conditions.

The term "cell product" or "cell products" as used herein refers to any and all substances made by and secreted from a cell, including but not limited to, protein factors (i.e. growth factors, differentiation factors, engraftment factors, cytokines, morphogens, proteases (i.e. to promote endogenous cell delamination, protease inhibitors), extracellular matrix components (i.e. fibronectin, etc.).

The term "therapeutically effective amount" means that amount of a therapeutic agent necessary to achieve a desired physiological effect (i.e. prevent or treat cartilage diseases, disorders and injuries).

As used herein, the term "pharmaceutically acceptable" means that the components, in addition to the therapeutic agent, comprising the formulation, are suitable for administration to the patient being treated in accordance with the present invention.

As used herein, the term "therapeutic component" means a component of the composition that exerts a therapeutic benefit when the composition is administered to a subject.

As used herein, the term "therapeutic protein" includes a wide range of biologically active proteins including, but not limited to, growth factors, enzymes, hormones, cytokines, inhibitors of cytokines, blood clotting factors, peptide growth and differentiation factors.

As used herein, the term "tissue" refers to an aggregation of similarly specialized cells united in the performance of a particular function.

As used herein, the terms "a" or "an" means one or more; at least one.

As used herein, the term "adjunctive" means jointly, together with, in addition to, in conjunction with, and the like.

As used herein, the term "co-administer" can include simultaneous or sequential administration of two or more agents.

As used herein, the term "agent" means an active agent or an inactive agent. By the term "active agent" is meant an agent that is capable of having a physiological effect when administered to a subject. Non-limiting examples of active agents include growth factors, cytokines, antibiotics, cells, conditioned media from cells, etc. By the term "inactive agent" is meant an agent that does not have a physiological effect when administered. Such agents may alternatively be called "pharmaceutically acceptable excipients". Non-limiting examples include time release capsules and the like.

The terms "parenteral administration" and "administered parenterally" are art-recognized and refer to modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intra-articulare, subcapsular, subarachnoid, intraspinal, epidural, intracerebral, intraosseous, intracartilagenous, and intrasternal injection or infusion.

As used herein, the term "enteral" administration means any route of drug administration that involves absorption of the drug through the gastrointestinal tract. Enteral administration may be divided into three different categories, oral, gastric, and rectal. Gastric introduction involves the use of a tube through the nasal passage or a tube in the abdomen leading directly to the stomach.

As used herein, the term "topical" administration means a medication that is applied to body surfaces such as the skin or mucous membranes to treat ailments via a large range of classes including but not limited to liquids, creams, foams, gels, lotions, salves and ointments.

The terms "sustained-release", "extended-release", "time-release", "controlled-release", or "continuous-release" as used herein means an agent, typically a therapeutic agent or drug, that is formulated to dissolve slowly and be released over time.

"Treatment," "treat," or "treating," as used herein covers any treatment of a disease or condition of a mammal, particularly a human, and includes: (a) preventing the disease or condition from occurring in a subject which may be predisposed to the disease or condition but has not yet been diagnosed as having it; (b) inhibiting the disease or condition, i.e., arresting its development; (c) relieving and or ameliorating the disease or condition, i.e., causing regression of the disease or condition; or (d) curing the disease or condition, i.e., stopping its development or progression. The population of subjects treated by the methods of the invention includes subjects suffering from the undesirable condition or disease, as well as subjects at risk for development of the condition or disease.

As used herein, a "wound" is any disruption, from whatever cause, of normal anatomy (internal and/or external anatomy) including but not limited to traumatic injuries such as mechanical (i.e. contusion, penetrating, crush), thermal, chemical, electrical, radiation, concussive and incisional injuries; elective injuries such as operative surgery and resultant incisional hernias, fistulas, etc.; acute wounds, chronic wounds, infected wounds, and sterile wounds, as well as wounds associated with disease states (i.e. ulcers caused by diabetic neuropathy or ulcers of the gastrointestinal or genitourinary tract). A wound is dynamic and the process of healing is a continuum requiring a series of integrated and interrelated cellular processes that begin at the time of wounding and proceed beyond initial wound closure through arrival at a stable scar. These cellular processes are mediated or modulated by humoral substances including but not limited to cytokines, lymphokines, growth factors, and hormones. In accordance with the subject invention, "wound healing" refers to improving, by some form of intervention, the natural cellular processes and humoral substances of tissue repair such that healing is faster, and/or the resulting healed area has less scaring and/or the wounded area possesses tissue strength that is closer to that of uninjured tissue and/or the wounded tissue attains some degree of functional recovery.

As used herein the term "standard animal model" refers to any art-accepted animal model for in which the compositions of the invention exhibit efficacy.

DETAILED DESCRIPTION

In accordance with the present invention there may be employed conventional molecular biology, microbiology, and recombinant DNA techniques within the skill of the art. Such techniques are explained fully in the literature. See, e.g., Sambrook et al, 2001, "Molecular Cloning: A Laboratory Manual"; Ausubel, ed., 1994, "Current Protocols in Molecular Biology" Volumes I-III; Celis, ed., 1994, "Cell Biology: A Laboratory Handbook" Volumes I-III; Coligan, ed., 1994, "Current Protocols in Immunology" Volumes I-III; Gait ed., 1984, "Oligonucleotide Synthesis"; Hames & Higgins eds., 1985, "Nucleic Acid Hybridization"; Hames & Higgins, eds., 1984,"Transcription And Translation"; Freshney, ed., 1986, "Animal Cell Culture"; IRL Press, 1986, "Immobilized Cells And Enzymes"; Perbal, 1984, "A Practical Guide To Molecular Cloning."

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

It must be noted that as used herein and in the appended claims, the singular forms "a," "and" and "the" include plural references unless the context clearly dictates otherwise.

Exemplary Therapeutic Uses

Degenerative Disc Disease (DDD)—is a common musculoskeletal disorder that is the major cause of lower back pain. It includes the more severe degenerative conditions lumbar scoliosis, disc herniation and spinal stenosis. It involves sequential degenerative changes to the intervertebral disc (IVD), the chief support structure of vertebrates that confers tensile strength, stability and flexibility to the spine. DDD in some form is fairly common, and is often associated with aging or simple wear and tear. By the age of fifty, 85 percent of the population will show evidence of IVD degeneration. In the U.S. alone, the cost of chronic lower back pain exceeds $30 billion annually.

Although in many cases DDD occurs as part of aging and is asymptomatic, in other cases it can be very painful. Pain occurs when the discs or the growth of bone spurs pinch and put pressure on the nearby nerve roots or spinal cord. In some cases, DDD is initiated by trauma, which can cause swelling, soreness and instability, promoting further deterioration and interfering with any potential healing in the area. Regardless of its cause, once IVD degeneration begins, there are no known treatments to stop it. This is because the disc itself does not have a direct blood supply, so its ability to repair itself is impaired.

Current treatments are mainly palliative or surgical and do not improve the ability of the disc to regain its original structure and function, although cell transplantation therapies offer the potential for regeneration in the future. Non-surgical (conservative) treatments include pain management and physical therapy. Surgical treatments include discectomy/fusion, disc prosthesis or posterior dynamic stabilization, all of which address the symptoms but not the cause of the disease and which often cause further complications in that they often accelerate degeneration in adjacent discs. Gene therapy, growth factors and cell transplantation, including transplantation of various multipotent cells, are currently being investigated. Injection of disc cells embedded in a biological hydrogel has suggested the possibility of regenerating an injured disc in early studies. It is an object of the invention to treat and/or reduce the inflammation associated with DDD.

Chondrodystrophies—are a group of diseases characterized by disturbance of growth and subsequent ossification of cartilage. It is an object of the invention to treat and/or reduce the inflammation associated with these conditions.

Arthritis—Osteoarthritis occurs when the cartilage covering bones (called articular cartilage) is thin and eventually completely wears out, resulting in a "bone against bone" joint, reduction in motion, and pain. Osteoarthritis primarily affects the joints exposed to high stress and is therefore generally considered the result of "wear and tear". It is often treated by arthroplasty, which is the replacement of the joint with a synthetic joint. It is an object of the present invention to prevent, treat and/or reduce the inflammation associated with osteoarthritis. Rheumatoid arthritis is a chronic inflammatory disorder that typically affects the small joints in the hands and feet. Unlike the damage seen in osteoarthritis, rheumatoid arthritis affects the lining of the joints, causing a painful swelling that can eventually result in bone erosion and joint deformity. Rheumatoid arthritis is an autoimmune disorder that occurs when the immune system attacks the body's own tissues. In addition to causing joint problems, rheumatoid arthritis sometimes can affect other organs of the body, such as the skin, eyes, lungs and blood vessels. Gouty arthritis is a type of arthritis that occurs when uric acid builds up in blood and causes inflammation in the joints. Acute gout is a painful condition that often affects only one joint. Chronic gout is repeated episodes of pain and inflammation. More than one joint may be affected. Psoriatic arthritis is a type of arthritic inflammation that occurs in about 15 percent of patients who have a skin rash called psoriasis. This particular arthritis can affect any joint in the body, and symptoms vary from person to person. Research has shown that persistent inflammation from psoriatic arthritis can lead to joint damage.

Traumatic rupture or detachment—The cartilage in joints, especially the knee, is frequently damaged and suffers traumatic rupture or detachment. This can be partially repaired through knee cartilage replacement therapy. It is an object of the present invention to treat and/or reduce the inflammation associated with traumatic rupture or detachment of cartilage.

Achondroplasty—Reduced proliferation of chondrocytes in the epiphyseal plate of long bones during infancy and childhood, resulting in dwarfism. It is an object of the invention to treat epiphyseal plate chondrocytes such that there is an increased proliferation of cells which will form normal amounts of cartilage.

Costochondritis—Inflammation of the costal cartilage in the ribs, which causes chest pain. It is an object of the present invention to treat and/or reduce the inflammation associated with costochondritis.

Intervertebral disc herniation—Asymmetrical compression of an intervertebral disc ruptures the sac-like disc, causing a herniation of its soft content. The hernia often compresses the adjacent nerves and causes back pain. It is an object of the present invention to treat and/or reduce the inflammation associated with intervertebral disc herniation.

Relapsing polychondritis destruction—This disease is believed to be an autoimmune disease affecting cartilage, especially of the nose and ears, causing disfiguration. In severe cases, death can occur by suffocation as the larynx loses its rigidity and collapses. It is an object of the present invention to treat and/or reduce the inflammation associated with relapsing polychondritis destruction.

Ankylosing spondylitis, or AS, is a fairly rare form of arthritis that primarily affects the spine, although other joints can become involved. It causes inflammation of the spinal joints (vertebrae) that can lead to severe, chronic pain and discomfort. In the most advanced cases, this inflammation can lead to new bone formation on the spine, causing the spine to fuse in a fixed, immobile position, sometimes creating a forward-stooped posture. This forward curvature of the spine is called kyphosis. It is an object of the present invention to treat and/or reduce the inflammation associated with ankylosing spondylitis.

Compositions and Methods of Making Compositions

Detailed information and methods on the preparation of AMP cell compositions, generation of ACCS, generation of pooled ACCS, detection of cytokines in non-pooled and pooled ACCS using ELISA, generation of PCS compositions, and generation of sustained-release CFS compositions can be found in U.S. Pat. Nos. 8,278,095, 8,058,066 and 8,088,732, each of which is incorporated herein by reference.

The invention provides for an article of manufacture comprising packaging material and a pharmaceutical composition of the invention contained within the packaging material, wherein the pharmaceutical composition comprises CFS compositions, including ACCS. The packaging material comprises a label or package insert that indicates that the CFS compositions, including ACCS, contained therein can be used for therapeutic applications such as, for example, preventing, treating and/or reducing inflammation associated with cartilage diseases, disorders and injuries.

Formulation, Dosage and Administration of CFS Compositions

Compositions comprising CFS compositions may be administered to a subject to provide various cellular or tissue functions, for example, to prevent, treat and/or reduce inflammation associated with cartilage diseases, disorders and injuries. As used herein "subject" may mean either a human or non-human animal.

Such compositions may be formulated in any conventional manner using one or more physiologically acceptable carriers optionally comprising excipients and auxiliaries. Proper formulation is dependent upon the route of administration chosen. The CFS compositions may be formulated as a liquid, cream, foam, gel, lotion, salve, and ointment, etc. The compositions may also be administered to the recipient in one or more physiologically acceptable carriers. Carriers for CFS compositions or AMP cells, AMP-NP cells or AMP-AF cells may include, but are not limited to, solutions of normal saline, phosphate buffered saline (PBS), lactated Ringer's solution containing a mixture of salts in physiologic concentrations, or cell culture medium.

In addition, one of skill in the art may readily determine the appropriate dose of the CFS compositions for a particular purpose. A preferred dose is in the range of about 0.1-to-1000 micrograms per square centimeter of applied area. Other preferred dose ranges are 1.0-to-50.0 micrograms/applied area. In a particularly preferred embodiment, it has been found that relatively small amounts of the CFS compositions are therapeutically useful. One exemplification of such therapeutic utility is the ability for ACCS (including pooled ACCS) to accelerate wound healing (for details see U.S. Publication No. 2006/0222634 and U.S. Pat. No. 8,187,881, both of which are incorporated herein by reference). One of skill in the art will also recognize that the number of doses to be administered needs also to be empirically determined based on, for example, severity and type of disease, disorder or injury being treated; patient age, weight, sex, health; other medications and treatments being administered to the patient; and the like. For example, in a preferred embodiment, one dose is sufficient to have a therapeutic effect (i.e. preventing, treating and/or reducing inflammation associated with cartilage diseases, disorders and injuries). Other preferred embodiments contemplate, 2, 3, 4, or more doses for therapeutic effect.

One of skill in the art will also recognize that number of doses (dosing regimen) to be administered needs also to be empirically determined based on, for example, severity and type of injury, disorder or condition being treated; patient age, weight, sex, health; other medications and treatments being administered to the patient; and the like. In addition, one of skill in the art recognizes that the frequency of dosing needs to be empirically determined based on similar criteria. In certain embodiments, one dose is administered every day for a given number of days (i.e. once a day for 7 days, etc.). In other embodiments, multiple doses may be administered in one day (every 4 hours, etc.). Multiple doses per day for multiple days are also contemplated by the invention.

In further embodiments of the present invention, at least one additional agent may be combined with the CFS compositions. Such agents may act synergistically with the CFS compositions of the invention to enhance the therapeutic effect. Such agents include but are not limited to growth factors, cytokines, chemokines, antibodies, inhibitors, antibiotics, immunosuppressive agents, steroids, anti-fungals, anti-virals or other cell types (i.e. stem cells or stem-like cells, for example AMP cells), extracellular matrix components such as aggrecan, versican hyaluronic acid and other glycosaminoglycans, collagens, etc. Inactive agents include carriers, diluents, stabilizers, gelling agents, delivery vehicles, ECMs (natural and synthetic), scaffolds, and the like. When the CFS compositions are administered conjointly with other pharmaceutically active agents, even less of the CFS compositions may be needed to be therapeutically effective.

CFS compositions may also be inserted into a delivery device in different forms. For example, the CFS compositions can be part of a solution contained in such a delivery device. As used herein, the term "solution" includes a pharmaceutically acceptable carrier or diluent. Pharmaceutically acceptable carriers and diluents include saline, aqueous buffer solutions, solvents and/or dispersion media. The use of such carriers and diluents is well known in the art. The solution is preferably sterile and fluid to the extent that easy syringability exists. Preferably, the solution is stable under the conditions of manufacture and storage and may optionally be preserved against the contaminating action of microorganisms such as bacteria and fungi through the use of, for example, parabens, chlorobutanol, phenol, ascorbic acid, thimerosal, and the like. Solutions of the invention can be prepared by incorporating the CFS compositions in a pharmaceutically acceptable carrier or diluent and, as required, other ingredients enumerated above.

The timing of administration of CFS compositions will depend upon the type and severity of the cartilage disease, disorder, or injury being treated. In one embodiment, the CFS compositions are administered as soon as possible after onset of symptoms, diagnosis or injury. In another embodiment, CFS compositions are administered more than one time following onset of symptoms, diagnosis or injury. In certain embodiments, where surgery is required, the CFS compositions are administered at surgery. In still other embodiments, the CFS compositions are administered at as well as after surgery. Such post-surgical administration may take the form of a single administration or multiple administrations.

Support matrices, scaffolds, membranes and the like into which the CFS compositions can be incorporated or embedded include matrices which are recipient-compatible and which degrade into products which are not harmful to the recipient. Detailed information on suitable support matrices, etc. can be found in U.S. Pat. Nos. 8,058,066 and 8,088,732, both of which are incorporated herein by reference.

One of skill in the art may readily determine the appropriate concentration, or dose, of the AMP cells, AMP-NP cells or AMP-AF cells for a particular purpose. The skilled artisan will recognize that a preferred dose is one that produces a therapeutic effect, such as preventing, treating and/or reducing inflammation associated with cartilage diseases, disorders and injuries, in a patient in need thereof. Of course, proper doses of the cells will require empirical determination at time of use based on several variables including but not limited to the severity and type of disease, injury, disorder or condition being treated; patient age, weight, sex, health; other medications and treatments being administered to the patient; and the like. An exemplary dose includes dose is in the range of about $0.25\text{-}2.0\times10^6$ cells. Other preferred dose ranges are $0.1\text{-}10.0\times10^6$ cells. In a particular preferred embodiment, it has been found that relatively small amounts of cells are effective. For example, only 1,000-100,000 AMP cells can be effective. One of skill in the art will also recognize that number of doses (dosing regimen) to be administered needs also to be empirically determined based on, for example, severity and type of disease, injury, disorder or condition being treated. In a preferred embodiment, one dose is sufficient. Other preferred embodiments contemplate, 2, 3, 4, or more doses.

The present invention provides a method of preventing, treating and/or reducing inflammation associated with cartilage diseases, disorders and injuries by administering to a subject AMP cells, AMP-NP cells or AMP-AF cells in a therapeutically effective amount. By "therapeutically effective amount" is meant the dose of AMP cells, AMP-NP cells or AMP-AF cells that is sufficient to elicit a therapeutic effect. Thus, the concentration of AMP cells, AMP-NP cells or AMP-AF cells in an administered dose unit in accordance with the present invention is effective in, for example, the preventing, treating and/or reducing inflammation associated with cartilage diseases, disorders and injuries.

In further embodiments of the present invention, at least one additional agent or treatment modality may be combined with the AMP cells, AMP-NP cells or AMP-AF cells to enhance preventing, treating and/or reducing inflammation associated with cartilage diseases, disorders and injuries. Such agents or treatment modalities may include, for example, cytokines, chemokines, antibodies, inhibitors, antibiotics, anti-fungals, anti-virals, immunosuppressive agents, and other cell types. When the AMP cells, AMP-NP cells or AMP-AF cells are administered conjointly with other pharmaceutically active agents, even less of the AMP cells, AMP-NP cells or AMP-AF cells may be needed to be therapeutically effective.

AMP cells, AMP-NP cells or AMP-AF cells can be administered by injection into a target site of a subject, preferably via a delivery device. In a specific embodiment, the delivery device contains a needle, e.g., a syringe, through which the AMP cells, AMP-NP cells or AMP-AF cells can be introduced into the subject at a desired location. Specific, non-limiting examples of administering cells to subjects may also include administration by intravenous injection, intraarterial injection, intramuscular injection, intrathecal injection, epidural injection, or infusion.

The timing of administration of AMP cells, AMP-NP cells or AMP-AF cells will depend upon the type and severity of the cartilage disease, disorder or injury being treated. In a specific embodiment, the AMP cells, AMP-NP cells or AMP-AF cells are administered as soon as possible after the disease or disorder is diagnosed or the injury occurs. In other specific embodiments, the AMP cells, AMP-NP cells or AMP-AF cells are administered more than one time following diagnosis or injury.

EXAMPLES

The following examples are put forth so as to provide those of ordinary skill in the art with a complete disclosure and description of how to make and use the compositions and methods of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees centigrade, and pressure is at or near atmospheric.

The following examples provide evidence of the anti-inflammatory and wound healing effects of ACCS is several different inflammatory disease states (mucosal, mucosal/infected; skin (intact and lesioned); and cutaneous wound/infected), thus providing strong evidence for the broad applicability of ACCS to prevent and/or treat inflammatory conditions.

Example 1

Inflammatory Model—Use of ACCS to Prevent Onset of Periodontal Disease in an Animal Model Objective: The aim of this study was to evaluate the preventive role of ACCS in *Porphyromonas gingivalis* (*P. gingivalis*)-induced experimental periodontitis in rabbits Methods: Eight New-Zealand White rabbits were distributed into 3 groups: 1. aUntreated (n=2), 2. aControl (unconditioned ACCS culture media) (n=3), and 3. aACCS (n=3). At baseline, all rabbits received silk ligatures bilaterally tied around mandibular second premolars under general anesthesia. The assigned test materials, ACCS or control, in volumes of 10 µL were topically applied to the ligated sites with a blunt needled-Hamilton Syringe from the time of ligature; control animals received ligature, but no treatment. Topical *P. gingivalis*-containing slurry (1 mL) was subsequently applied to induce the periodontal inflammation. The application of test materials and *P. gingivalis* continued for 6 weeks on an every-other-day schedule. At 6 weeks, following euthanasia, the mandibles were surgically harvested. Morphometric, radiographic and histologic evaluations were performed.

Results: Macroscopic evaluations including soft tissue assessments, crestal bone and infrabony measurements showed significant periodontal breakdown induced by *P. gingivalis* in control and no treatment groups at 6 weeks compared to historical ligature-alone groups (p=0.05, p=0.03, respectively). ACCS application significantly inhibited soft tissue inflammation and prevented both crestal bone loss and infrabony defect formation compared to untreated and control groups (p=0.01, p=0.05, respectively). Histologic assessments and histomorphometric measurements supported the clinical findings; ACCS treated animals demonstrated significantly less inflammation in soft tissue and less bone loss compared to the untreated and control groups (p=0.05).

Conclusions: Topical ACCS application prevents periodontal inflammatory changes and bone loss induced by *P. gingivalis* as shown both at clinical and histopathological level. ACCS has potential as a therapeutic approach for the prevention of periodontal diseases Example 2

Inflammatory Model—Use of ACCS to Stop Progression of or Reverse Periodontal Disease in an Animal Model Objective: The aim of this study was to evaluate the therapeutic actions of ACCS in the treatment of periodontitis induced by *P. gingivalis*.

Methods: The study was conducted using a two-phase rabbit periodontitis protocol: 1—Disease induction (6 weeks) and 2—Treatment (6 weeks). Periodontal disease was induced in 16 New-Zealand White rabbits by every-other-day application of topical *P. gingivalis* to ligatured mandibular premolars. At the end of Phase 1, 4 randomly selected rabbits were sacrificed to serve as the baseline disease group. For Phase 2, the remaining 12 rabbits were distributed into 3 groups (n=4), 1—Untreated, 2—Control (unconditioned ACCS culture media) and 3—ACCS treatment. At the end of Phase 2, morphometric, radiographic and histologic evaluations were performed on harvested mandibles.

Results: The baseline disease group exhibited experimental periodontitis evidenced by tissue inflammation and bone loss. At the end of Phase 2, the untreated group showed significant disease progression characterized by increased soft and hard tissue destruction (p=0.05). The tissue inflammation and bone loss was significantly reduced by topical ACCS compared to baseline disease and untreated groups (p=0.05; p=0.002, respectively). The control treatment also arrested disease progression compared to untreated group (p=0.01), but there was no improvement in periodontal health compared to baseline disease (p=0.4). Histopathological assessments revealed similar findings; ACCS stopped the progression of inflammatory process (p=0.003) and reversed bone destruction induced by *P. gingivalis* (p=0.008). The ACCS-treated group had minimal osteoclastic activity limited to crestal area compared to untreated and control groups, which showed a profound osteoclastogenic activity at the bone crest as well as at interproximal sites.

Conclusions: Topical application of ACCS stopped the progression of periodontal inflammation and resulted in tissue regeneration in rabbit periodontitis indicating its potential therapeutic efficacy.

Example 3

Evaluate the Efficacy of Topically Applied ACCS to Inhibit Irritant 12-O-tetradecanoylphorbol-3-acetate (TPA) Skin Inflammation in Mice Method: Topical treatment was given twice daily to the following groups: 1. aTPA+topical control; 2. aTPA+ACCS; 3. aTPA+clobetasol 0.05 topical solution (the strongest available topical corticosteroid); 4. aACCS alone; 5. aNo treatment (the other untreated ear was measured). The endpoints for the study were ear thickness and ear weight at the end of the experiment. The thicker the ear and the more it weighs correlates with the degree of inflammation.

Results: Topically applied ACCS was effective at reducing the inflammation induced by TPA. The anti-inflammatory activity of topical ACCS reached the same level as clobetasol (a class 1 potent topical corticosteroid) by 3 days after beginning application.

Example 4

Evaluate the Efficacy of Intralesional Injection of ACCS to Inhibit Irritant (TPA) Skin Inflammation in Mice Method: Intralesional injection into the ear was given once daily to the following groups: 1. aTPA+intralesional control; 2. aTPA+intralesional ACCS; 3. aTPA+intralesional kenalog (10 mg/ml) (a potent intralesional corticosteroid); 4. aACCS intralesional injection alone; 5. aSaline sham injections to the normal untreated ear. The endpoints for the study were ear thickness and ear weight at the end of the experiment. The thicker the ear and the more it weighs correlates with the degree of inflammation.

Results: Intralesional injection of ACCS was effective at reducing the inflammation induced by TPA at all time points beginning on day 2 of daily injections. Intralesional kenalog (10 mg/ml) injections induced a hematoma at the site of injection, which led to some inflammation and that is why there is not a substantial difference in ear thickness when comparing TPA+kenalog with TPA+control.

Conclusions: Intralesional ACCS did reduce skin inflammation but the topically applied ACCS in Example 1 above had a more potent effect. There was no difference in ear weight using either ACCS or intralesional kenalog compared with TPA+control.

Example 5

Effects of ACCS in an Animal Model of Chronic Wound Healing

An art-accepted animal model for chronic granulating wound was used to study the effects of ACCS on chronic wound healing (Hayward P G, Robson M C: Animal models of wound contraction. In Barbul A, et al: Clinical and Experimental Approaches to Dermal and Epidermal Repair: Normal and Chronic Wounds. John Wiley & Sons, New York, 1990.).

Results: ACCS was effective in not allowing proliferation of tissue bacterial bioburden. ACCS allowed accelerated healing of the granulating wound significantly faster than the non-treated infected control groups (Franz, M., et al., ePlasty Vol. 8, pp. 188-199, Apr. 11, 2008).

Example 6

Effect of ACCS on Proliferation of Human Nucleus Pulposus Cells and Human Annulus Fibrosus Cells Objective: The purpose of this experiment was to evaluate the effect of ACCS on proliferation of human nucleus pulposus cells and human annulus fibrosus cells.

Method: A WST-8 proliferation assay (Cayman Chemicals, #10010199) was used to assess the effects of ACCS on proliferation of human nucleus pulposus cells and human annulus fibrosus cells. The cells were treated with either 100% ACCS or 50% ACCS diluted in either NP cell growth medium or basal medium.

Results: In both the 100% and 50% ACCS-treated samples, the cells exhibited proliferation equal to or greater than that seen with NP growth medium. The negative control of basal medium+EGF exhibited the lowest level of proliferation.

These data indicate that ACCS treatment may increase the rate of proliferation of intervertebral disc cells.

Example 7

Ability of ACCS to Down-Regulate Notch Pathway Activation

Objective: The purpose of this experiment was to evaluate the ability of ACCS to down-regulate notch pathway activation. The notch pathway is activated in degenerative disc disease. When this pathway is activated, Hey1, which is downstream of notch1, expression increases.

Method: Human nucleus pulposus cells and human annulus fibrosus cells were treated with TNFα plus or minus ACCS. This treatment turned on the notch pathway in both cell types as demonstrated by an increase in Hey1 expression. This experiment was designed to determine if ACCS can down-regulate notch activation in human nucleus pulposus cells and human annulus fibrosus cells treated with TNFα.

Results: ACCS was able to down-regulate the response of human nucleus pulposus cells and human annulus fibrosus cells to TNF-α stimulation as demonstrated by a decrease in Hey1expression as compared to the stimulated control medium. However, once the notch pathway is activated, it does not appear that ACCS can turn it off quickly.

Example 8

Ability of ACCS to Protect Human Nucleus Pulposus Cells and Human Annulus Fibrosus Cells from Apoptosis Objective: Apoptosis is believed to be a significant contributing factor for degenerating disc disease. In this experiment, ACCS was evaluated for its ability to protect both annulus fibrosis cells and nucleus pulposus cells against Staurosporin-induced apoptosis.

Method: Human nucleus pulposus cells and human annulus fibrosus cells were grown in 100% growth media or 50% growth media/ACCS overnight and then treated with Staurosporin at multiple concentrations to induce apoptosis.

Results: Using a Caspase-Glo 3/7 assay (Promega #G8093) it was shown that at higher Staurosporin concentrations (2.5-10 µM) ACCS (50% final concentration) reduced the apoptotic effect in both cell types.

Example 9

Generation of AMP-NP Cells and AMP-AF Cells

Method: AMP cells are cultured under specific conditions such that they develop either an NP cell-like phenotype or an AF cell-like phenotype. An NP cell-like phenotype includes secretion of the proper proteoglycan-to-collagen ratio. Specifically, the ratio should be 27:1. aAnother NP cell-like phenotype is expression of Collagen II, aggrecan and Sox9. aAn AF cell-like phenotype includes cells which appear fibroblastic and which secrete Collagen I, Collagen II, elastin and high GAG production. For example, Boeuf and Richter (Stem Cell Research & Therapy 2010, 1:31) describe numerous methodologies used to culture MSCs to induce chondrogenic differentiation. AMP cells can be subjected to any one of these methods or other methods familiar to skilled artisans to induce the desired NP cell or AF cell-like phenotype.

Conclusion: ACCS has a strong anti-inflammatory effect when applied to skin.

Example 10

Generation of ACCS-NP and ACCS-AF Conditioned Medium

Method: AMP-NP cells or AMP-AF cells are cultured for a period of time and the conditioned culture medium, termed ACCS-NP or ACCS-AF, is collected and used in the claimed methods.

Example 11

Effects of ACCS, ACCS-NP and ACCS-AF in Animal Models of Cartilage Diseases, Disorders and Injuries Method: Art-accepted animal models for cartilage diseases, disorders and injuries are used to test the effects of ACCS, ACCS-NP and ACCS-AF in preventing, treating and/or reducing the inflammation associated with such conditions. For example, Benz, et al. (Eur Spine J, 2012, 21:1758-1768) describe a sheep model using autologous and/or allogenic repair of intervertebral disc after massive disc injury. Bergknut, et al. (Spine, 2012, 37(5):351-358) describe a canine model to investigate whether spontaneous intervertebral disc degeneration occurring in both chondrodystrophic and nonchondrodystrophic dogs can be used as a valid translational model for human research. Ghosh, et al. (J Neurosurg: Spine, 2012, 16(5):479-488) describe a sheep model of degenerative disc disease which utilizes immunoselected STRO-3+mesenchymal precursor cells to restore extracellular matrix in the disc. Chu, et al. (Tissue Eng, 2010, 16(1): 105-115) review several different animal models for cartilage regeneration and repair. Skilled persons recognize that other animal models known in the art may also be used.

Example 12

Effects of AMP Cells, AMP-NP Cells and AMP-AF Cells in Animal Models of Cartilage Diseases, Disorders and Injuries Method: Art-accepted animal models for cartilage diseases, disorders and injuries are used to test the effects of AMP cells, AMP-NP cells and AMP-AF cells in preventing, treating and/or reducing the inflammation associated with such conditions. For example, Benz, et al. (Eur Spine J, 2012, 21:1758-1768) describe a sheep model using autologous and/or allogenic repair of intervertebral disc after massive disc injury. Bergknut, et al. (Spine, 2012, 37(5):351-358) describe a canine model to investigate whether spontaneous intervertebral disc degeneration occurring in both chondrodystrophic and nonchondrodystrophic dogs can be used as a valid translational model for human research. Ghosh, et al. (J Neurosurg: Spine, 2012, 16(5):479-488) describe a sheep model of degenerative disc disease which utilizes immunoselected STRO-3+mesenchymal precursor cells to restore extracellular matrix in the disc. Chu, et al. (Tissue Eng, 2010, 16(1): 105-115) review several different animal models for cartilage regeneration and repair. Skilled persons recognize that other animal models known in the art may also be used.

The present invention may be embodied in other specific forms without departing from the spirit or essential attributes thereof Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

Throughout the specification various publications have been referred to. It is intended that each publication be incorporated by reference in its entirety into this specification

What is claimed is:

1. A method for reducing the inflammation associated with degenerative disc disease in a patient in need thereof comprising administering to the patient a therapeutically effective amount of a composition selected from the group consisting of Amnion-derived Cellular Cytokine Solution (ACCS), ACCS-nucleus pulposus (NP) and ACCS-annulus fibrosus (AF).

2. A method for promoting the growth or enhancing the survival of nucleus pulposus (NP) cells in a degenerating intervertebral disc comprising administering to the degenerating intervertebral disc a therapeutically effective amount of a composition selected from the group consisting of ACCS, ACCS-NP and ACCS-AF.

\* \* \* \* \*